US012735370B2

(12) United States Patent
Yogo et al.

(10) Patent No.: US 12,735,370 B2
(45) Date of Patent: Sep. 15, 2026

(54) CARBON DIOXIDE SEPARATION, COLLECTION, AND UTILIZATION SYSTEM AND CARBON DIOXIDE SEPARATION, COLLECTION, AND UTILIZATION METHOD

(71) Applicant: Research Institute of Innovative Technology for the Earth, Kyoto (JP)

(72) Inventors: Katsunori Yogo, Kyoto (JP); Masahiro Seshimo, Kyoto (JP)

(73) Assignee: Research Institute of Innovative Technology for the Earth, Kyoto (JP)

( * ) Notice: Subject to any disclaimer, the term of this patent is extended or adjusted under 35 U.S.C. 154(b) by 483 days.

(21) Appl. No.: 18/563,007

(22) PCT Filed: May 19, 2022

(86) PCT No.: PCT/JP2022/020775
§ 371 (c)(1),
(2) Date: Nov. 21, 2023

(87) PCT Pub. No.: WO2022/264745
PCT Pub. Date: Dec. 22, 2022

(65) Prior Publication Data

US 2024/0270663 A1 Aug. 15, 2024

(30) Foreign Application Priority Data

Jun. 18, 2021 (JP) ................................ 2021-101670

(51) Int. Cl.
*C07C 1/12* (2006.01)
*B01D 53/22* (2006.01)

(52) U.S. Cl.
CPC .............. *C07C 1/12* (2013.01); *B01D 53/228* (2013.01); *B01D 53/229* (2013.01); *B01D 2053/223* (2013.01)

(58) Field of Classification Search
CPC ..... C07C 1/12; C07C 29/1518; B01D 53/228; B01D 53/229; B01D 2053/223;
(Continued)

(56) References Cited

U.S. PATENT DOCUMENTS 8,999,279 B2 * 4/2015 Wright ............... B01D 53/0423 423/230
9,266,052 B2 * 2/2016 Wright .................. A01G 33/00
(Continued)

FOREIGN PATENT DOCUMENTS

CN 107744722 A * 3/2018 ............. B01D 53/73
JP 2018008940 A * 1/2018 ........... B01D 61/362
(Continued)

*Primary Examiner* — Stephen Hobson
(74) *Attorney, Agent, or Firm* — Stinson LLP

(57) ABSTRACT

A carbon dioxide collection and utilization system including: a regeneration unit that produces, from a solid material in or on which carbon dioxide is absorbed or adsorbed, a gas containing the carbon dioxide, and regenerates the solid material; a reactor into which the gas containing the carbon dioxide produced in the regeneration unit and hydrogen are introduced and which produces steam and at least one selected from the group consisting of synthetic fuel, methane, and methanol; and a steam introduction line that introduces at least part of the steam produced in the reactor, into the regeneration unit.

7 Claims, 2 Drawing Sheets

(58) Field of Classification Search

CPC .... B01D 53/1475; B01D 53/04; B01D 53/14; B01D 53/22; B01D 53/62; B01D 53/82; B01D 53/96; B01D 69/10; B01D 69/12; B01D 71/02; Y02C 20/40; Y02P 20/151; C01B 32/50

See application file for complete search history.

(56) References Cited

U.S. PATENT DOCUMENTS 9,283,510 B2* 3/2016 Lackner ................. B01D 53/02
9,321,655 B2* 4/2016 Singh ...................... C01B 3/025
9,387,433 B2* 7/2016 Lackner ................. B01D 53/62
9,878,285 B2* 1/2018 Schraven .............. C07C 227/18
2016/0039724 A1* 2/2016 Naterer .............. B01D 53/1425 422/162
2016/0074803 A1* 3/2016 Gebald .............. B01D 53/0415 95/139
2016/0153316 A1* 6/2016 Bergins ..................... C10L 3/00 518/703
2016/0214910 A1* 7/2016 King ......................... C01B 3/36
2018/0015407 A1* 1/2018 Vittenet ............. B01J 20/28057
2019/0359894 A1* 11/2019 Heidel ................. B01D 53/343
2021/0229032 A1* 7/2021 Yamamoto ............. B01D 53/62
2024/0270663 A1* 8/2024 Yogo ...................... B01D 53/62
2026/0132094 A1* 5/2026 Picard ...................... B01J 35/77

FOREIGN PATENT DOCUMENTS

JP 2019089675 A * 6/2019
JP 2022022908 A * 2/2022
JP 2022163279 A * 10/2022
JP 2023147421 A * 10/2023
WO WO-2017183388 A1 * 10/2017 ............. F02M 21/04
WO WO-2019073867 A1 * 4/2019 ............. B01D 53/82
WO 2020090806 A1 7/2020
WO WO-2021246318 A1 * 12/2021 ............. B01D 53/78

* cited by examiner

CARBON DIOXIDE SEPARATION, COLLECTION, AND UTILIZATION SYSTEM AND CARBON DIOXIDE SEPARATION, COLLECTION, AND UTILIZATION METHOD

REFERENCE TO RELATED APPLICATIONS

This application is the 371 U.S. national stage application of International Patent Application No. PCT/JP2022/020775, filed May 19, 2022, which claims the benefit of Japanese Patent Application No. 2021-101670, filed Jun. 18, 2021, the entire disclosures of which are incorporated herein by reference.

TECHNICAL FIELD

The present invention relates to a collection and utilization system and a collection and utilization method of carbon dioxide.

BACKGROUND ART

There has been increasing need in recent years to reduce greenhouse gases, which necessitates urgent development of technologies of collecting carbon dioxide from exhaust gases produced in power plants, steel plants, cement plants, and the like.

For example, Patent Literature 1 discloses a carbon dioxide collection method including: a step of bringing a carbon dioxide adsorbent in the form of particles into contact with a gas to be processed which contains carbon dioxide, to allow the carbon dioxide adsorbent to absorb the carbon dioxide contained in the gas to be processed; and a step of bringing the carbon dioxide adsorbent which has adsorbed carbon dioxide into contact with superheated steam, to allow the carbon dioxide to be desorbed from the carbon dioxide adsorbent, thereby to regenerate the carbon dioxide adsorbent and to collect the desorbed carbon dioxide, wherein the saturation temperature of the superheated steam brought into contact with the carbon dioxide adsorbent is equal to or lower than the temperature of the carbon dioxide adsorbent coming in contact with the superheated steam, and without being subjected to a drying step, the regenerated carbon dioxide adsorbent is utilized again for adsorption of carbon dioxide.

Patent Literature 2 teaches a methanol production method including steps of: supplying a raw material gas containing carbon dioxide and hydrogen, into a first space on the pre-permeation side of a separation membrane reactor which includes the first space, a steam separation membrane, a second space on the post-permeation side, and a catalyst placed in the first space, to allow a conversion reaction of the raw material gas into methanol to proceed by the action of the catalyst; circulating a sweep gas in the second space, thereby to remove reaction heat generated along with the conversion reaction and discharge steam which is a by-product of the conversion reaction and has permeated through the steam separation membrane, from the second space; cooling a non-permeated fluid containing methanol produced by the conversion reaction and unreacted gas, to condense the methanol, thereby to separate the methanol from the unreacted gas; and circulating the unreacted gas in the first space.

CITATION LIST

Patent Literature

Patent Literature 1: International Publication WO2020-90806

Patent Literature 2: Japanese Laid-Open Patent Publication No. 2018-8940

SUMMARY OF INVENTION

Technical Problem

A carbon dioxide collection and utilization system and a carbon dioxide collection and utilization method which are excellent in energy efficiency are to be provided.

Solution to Problem

One aspect of the present invention relates to a carbon dioxide collection and utilization system, including: a regeneration unit that produces, from a solid material in or on which carbon dioxide is absorbed or adsorbed, a gas containing the carbon dioxide, and regenerates the solid material; a reactor into which the gas containing the carbon dioxide produced in the regeneration unit and hydrogen are introduced and which produces steam and at least one selected from the group consisting of synthetic fuel, methane, and methanol; and a steam introduction line that introduces at least part of the steam produced in the reactor, into the regeneration unit.

Another aspect of the present invention relates to a carbon dioxide collection and utilization method, including: a preparation step of preparing a solid material in or on which carbon dioxide is absorbed or adsorbed, a regeneration step of producing from the solid material in or on which carbon dioxide is absorbed or adsorbed, a gas containing the carbon dioxide and regenerating the solid material; and a reaction step of allowing the gas containing the carbon dioxide to react with hydrogen, to produce steam and at least one selected from the group consisting of synthetic fuel, methane, and methanol, wherein the regeneration step includes brining at least part of the steam into contact with the solid material in or on which carbon dioxide is absorbed or adsorbed.

Advantageous Effects of Invention

According to the present invention, the steam produced by the hydrogenation reaction of carbon dioxide, which is an exothermic reaction, is used to regenerate the solid material. It is therefore possible to provide a carbon dioxide collection and utilization system and a carbon dioxide collection and utilization method which are excellent in energy efficiency.

While the novel features of the invention are set forth particularly in the appended claims, the invention, both as to organization and content, will be better understood and appreciated, along with other objects and features thereof, from the following detailed description taken in conjunction with the drawings.

DESCRIPTION OF EMBODIMENTS

Figure 1:
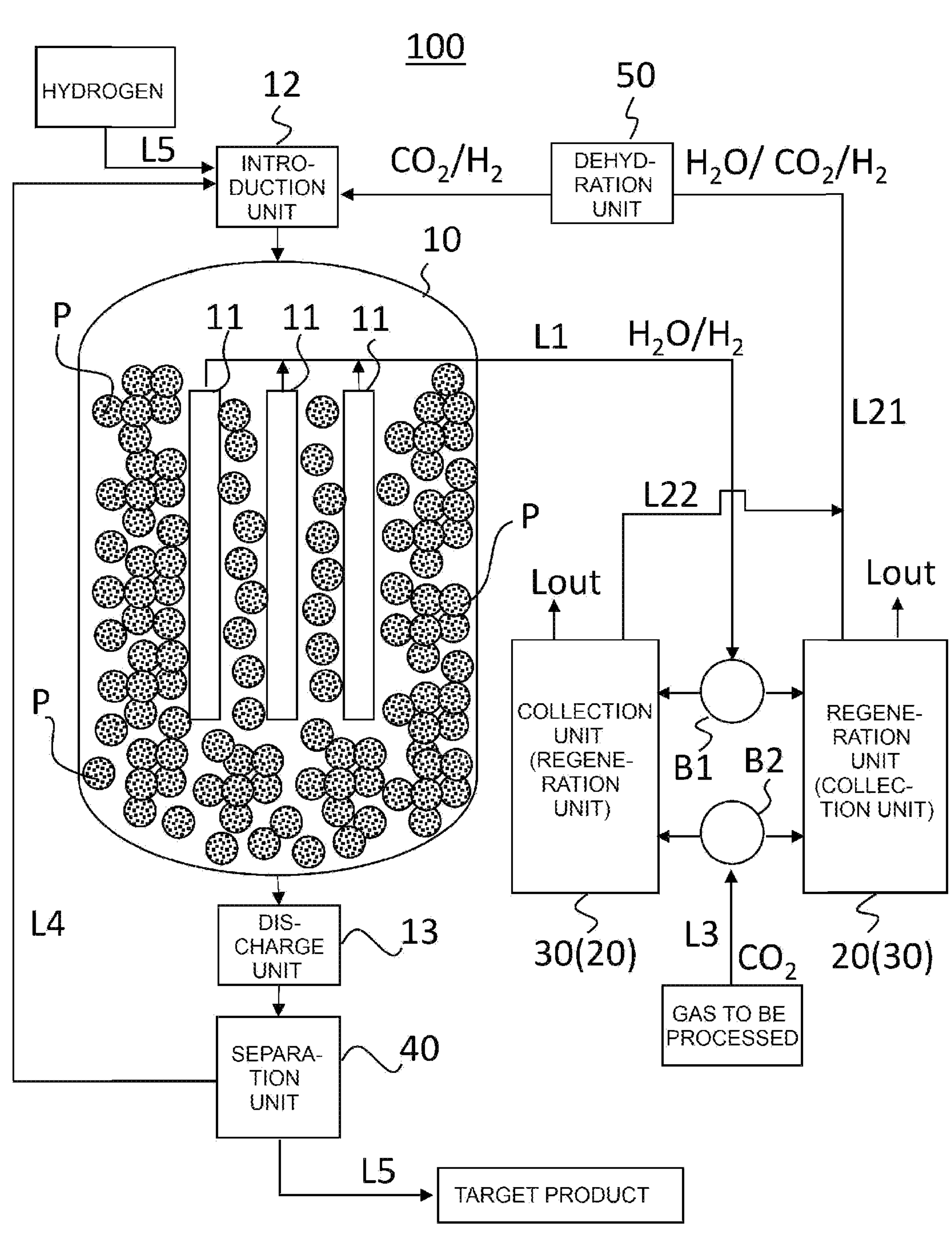
FIG. 1 A block diagram illustrating a configuration of an example of a carbon dioxide collection and utilization system according to an embodiment of the present invention.

An example of a carbon dioxide collection and utilization system according to an embodiment of the present invention is a system excellent in energy utilization efficiency that combines a carbon dioxide collection system with a hydrogenation reaction of the collected carbon dioxide. Regarding the carbon dioxide collection system, the construction thereof in thermal power plants, cement factories, steel plants, chemical factories, and the like has been examined. There have been also developed the FT (Fischer-Tropsch) synthesis to synthesize synthetic fuels by chemically reducing the collected carbon dioxide, and technologies to synthesize methane, methanol, and the like by hydrogenating carbon dioxide. The direct air capture (DAC) which is a technology to collect carbon dioxide from ambient air and uses it for business is also attracting attention.

In the carbon dioxide collection system, a method of allowing carbon dioxide to be absorbed in or adsorbed on a solid material, to separate the carbon dioxide is promising. The solid material has durability suited for repeated use. The solid material in or on which carbon dioxide is absorbed or adsorbed is regenerated by bringing it into contact with steam in the regeneration unit, and used repeatedly. In the regenerating unit, the solid material is heated by steam, through which a gas containing carbon dioxide is taken out and the solid material is regenerated.

When steam is introduced into the regeneration unit, the carbon dioxide partial pressure (carbon dioxide concentration) significantly decreases as compared to that at the surface of the solid material. Such a difference in carbon dioxide partial pressure acts as a driving force, to cause the carbon dioxide that has been absorbed in or adsorbed on the solid material to diffuse into the steam. Thus, the carbon dioxide is desorbed from the solid material, and the solid material is regenerated.

The steam may be superheated steam. Due to its low relative humidity as compared to saturated steam, when superheated steam is used, condensed water is less likely to adhere onto the surface of the solid material. The inside of the regeneration unit may be a reduced pressure atmosphere. In a reduced pressure atmosphere, the temperature of the superheated steam becomes less than 100° C. (e.g., 60 to 80° C.). The temperature of the superheated steam may be controlled to be equal to or below the temperature of the solid material, but may be higher than the temperature of the solid material. The temperature of the superheated steam may be, for example, 20 to 30° ° C. higher than the temperature of the solid material.

The saturation temperature of the superheated steam may be equal to or below the temperature of the solid material. In this case, no condensation of steam occurs on the surface of the solid material or the amount of condensation is suppressed to be very small, which eliminates the necessity of drying the solid material after regeneration. When the necessity of drying the solid material is eliminated, the downsizing of the carbon dioxide collection and utilization system and the reduction of equipment costs also become easy.

The solid material may be, for example, a porous material or a honeycomb supporting an amine compound, and the like, but is not limited thereto. Examples of the porous material include activated carbon, activated alumina, silica, silica alumina, titania, zirconia, and cordierite.

The gas containing carbon dioxide produced in the regeneration unit is sent to a reactor together with hydrogen, and reacts with hydrogen in the reactor, to produce a target product and steam. This reaction is an exothermic reaction, and the steam can be used as a heat source. In a reaction between carbon dioxide and hydrogen, at least one selected from the group consisting of synthetic fuel, methane, and methanol is produced as a target product. The synthetic fuel refers to a fuel that is liquid at ordinary temperature and ordinary pressure, such as gasoline having 5 to 12 carbon atoms and diesel oil having 12 to 18 carbon atoms, and in particular, is preferably a liquid hydrocarbon fuel mainly composed of a hydrocarbon having 5 to 10 carbon atoms.

In the carbon dioxide collection and utilization system according to the present embodiment, steam that can be used as a heat source is extracted from the reactor, and at least part of the steam is introduced into the regeneration unit. That is, the carbon dioxide collection and utilization system according to the present embodiment includes a steam introduction line for introducing at least part of the steam produced in the reactor into the regeneration unit.

The first advantage of the present embodiment is that the heat-stored steam produced by the hydrogenation reaction of carbon dioxide can be used to regenerate the solid material, and thus, excellent energy efficiency can be achieved. In the regeneration unit, the solid material in or on which carbon dioxide is absorbed or desorbed is efficiently heated by the steam, which facilitates the desorption of the carbon dioxide from the solid material. This can reduce the energy necessary to collect the carbon dioxide.

Here, the reactor is preferably a membrane reactor including a first space on the pre-permeation side into which the gas containing carbon dioxide and the hydrogen are introduced, a steam separation membrane, and a second space on the post-permeation side. The steam separation membrane is arranged so as to isolate the first space from the second space. The steam separation membrane is, for example, an inorganic composite and includes a porous support and an inorganic membrane supported thereon.

Examples of the inorganic membrane include a zeolite membrane, a silica membrane, and a carbon membrane. The thickness of the inorganic membrane is, for example, 0.5 μm to 10 μm. The porous support is, for example, a cylindrical body having a first surface and a second surface, in which the first surface and the second surface communicate with each other through pores, the first space communicates at the first surface with the pores, and the second surface communicates at the second surface with the pores. Examples of the material of the porous support include silica, alumina, zirconia, cordierite, and stainless steel (SUS).

In the first space, a catalyst that promotes the hydrogenation reaction of carbon dioxide may be placed. The catalyst, for example, may be packed in the first space, or may be supported on the steam separation membrane on the first space side thereof. Examples of the catalyst that promotes the hydrogenation reaction of carbon dioxide include iron, copper, palladium, zinc oxide, zirconia, gallium oxide, and composites thereof.

In the first space on the pre-permeation side of the membrane reactor, the hydrogenation reaction of carbon dioxide proceeds, to produce a target product and steam. For example, the reaction formula of the FT synthesis is as follows. The target product (e.g., liquid hydrocarbon) is collected from the first space.

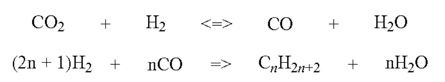

$$CO_2 + H_2 <=> CO + H_2O$$

$$(2n+1)H_2 + nCO => C_nH_{2n+2} + nH_2O$$

On the other hand, the produced steam passes through the steam separation membrane and moves into the second space on the post-permeation side. The second advantage of the present embodiment is that the steam, which is a byproduct, moves into the second space and is removed from the first space, and the equilibrium movement promotes the reaction between carbon dioxide and hydrogen, leading to an improve conversion rate of carbon dioxide.

However, since water and hydrogen have similar molecular sizes, part of the hydrogen introduced as a raw material into the first space also permeates the steam separation membrane and moves into the second space. That is, the steam extracted from the second space contains hydrogen. Hydrogen is a valuable resource for efficiently operating a carbon dioxide utilization system, and the reuse thereof is desired.

The third advantage of the present embodiment is that the hydrogen that has inevitably moved into the second space is introduced into the steam introduction line together with the heat-stored steam, and introduced into the regeneration unit. In this case, the gas containing carbon dioxide produced in the regeneration unit is mixed with the hydrogen introduced from the second space. The hydrogen mixed with the gas containing carbon dioxide is sent to the reactor together with the carbon dioxide and reused as a raw material. Therefore, the effective utilization rate of hydrogen is considerably increased.

As for the steam permeation rate of the steam separation membrane, the higher the rate is, the more desirable, but the amount of the hydrogen that inevitably moves into the second space also increases. However, the hydrogen that has moved into the second space is introduced into the regeneration unit through the steam introduction line and eventually returned to the reactor, and therefore, the hydrogen loss is restricted. The steam permeation rate of the steam separation membrane may be, for example, $1\times10^{-7}$ mol/(s·Pa·$m^2$) or more, or may exceed $1\times10^{-6}$ mol/(s·Pa·$m^2$).

The carbon dioxide collection and utilization system according to the present embodiment may further include a dehydration unit that removes the steam from the gas containing carbon dioxide before being introduced into the reactor. The dehydration unit may have, for example, a function of cooling the gas containing carbon dioxide. When cooled, the steam turns into liquid, and carbon dioxide and hydrogen both in the form of gas are collected. A mixed gas of the collected carbon dioxide and hydrogen is introduced into the reactor. The dehydration unit may have any configuration.

The carbon dioxide collection and utilization system according to the present embodiment may further include a carbon dioxide collection unit that brings a gas to be processed which contains carbon dioxide into contact with the solid material, to allow the carbon dioxide to be absorbed in or adsorbed on the solid material. The solid material in or on which carbon dioxide has been absorbed or adsorbed in the carbon dioxide collection unit is supplied to the regeneration unit. In this way, a carbon dioxide collection and utilization system excellent in energy utilization efficiency that combines a carbon dioxide collection system and a target product production using the collected carbon dioxide as a raw material can be constructed.

The carbon dioxide collection unit may also serve as the regeneration unit. That is, the regeneration unit may have a function of the carbon dioxide collection unit, and the carbon dioxide collection unit may have a function of the regeneration unit. For example, after carbon dioxide is adsorbed on a solid material packed in the carbon dioxide collection unit, steam may be introduced into the carbon dioxide collection unit, so that the carbon dioxide collection unit can be used as the regeneration unit.

The gas to be processed is produced, for example, in large quantities as a gas containing carbon dioxide in thermal power plants, cement factories, steel plants, chemical factories, and the like. For example, in a steel plant, a gas containing carbon dioxide with high concentration is produced as a blast furnace gas or converter gas. The gas to be processed may be combustion gas of biomass, and may be air in the atmosphere, closed space, or indoor space.

Figure 2:
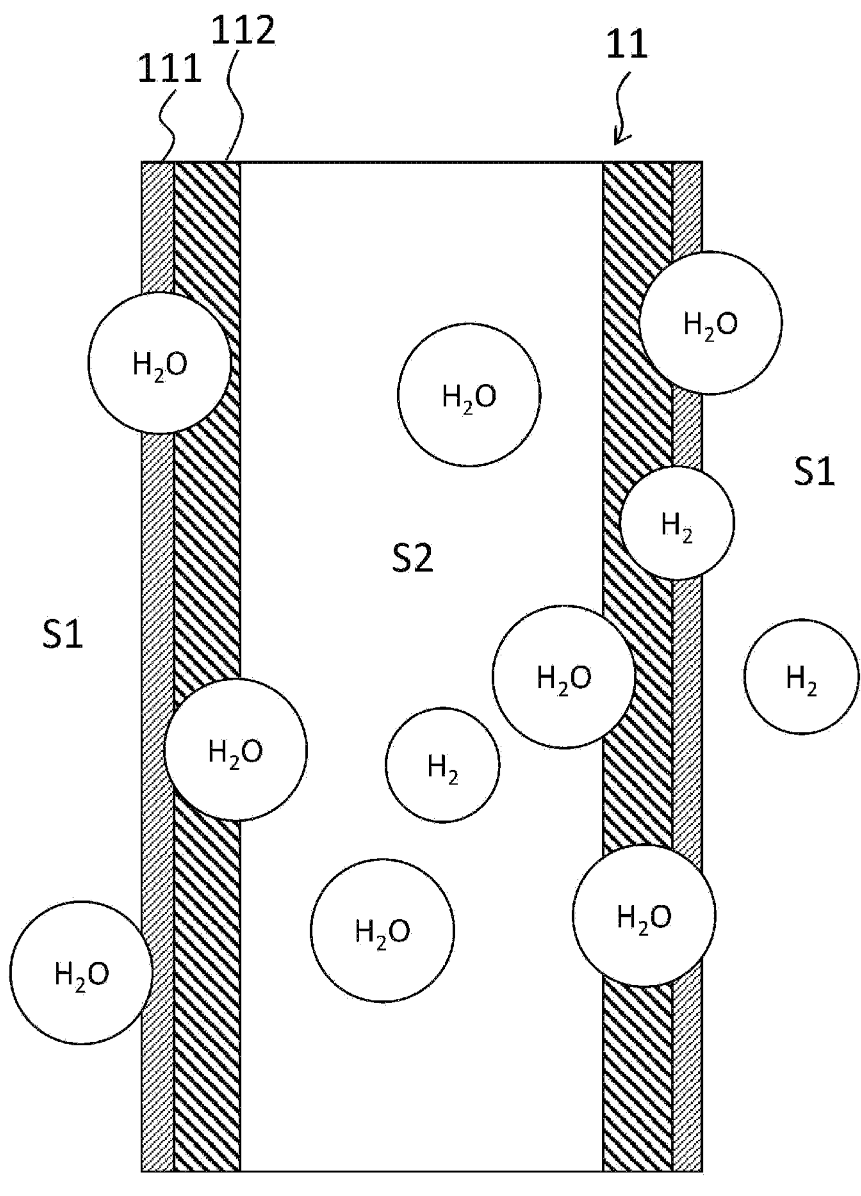
FIG. 2 A conceptual diagram showing a configuration of a steam separation membrane included in a membrane reactor equipped in the system of FIG. 1.

In the following, an example of the carbon dioxide collection and utilization system and an example of the collection and utilization method according to the present embodiment will be specifically described with reference to the drawings. FIG. 1 is a block diagram illustrating a configuration of an example of the carbon dioxide collection and utilization system. FIG. 2 is a conceptual diagram showing a configuration of the steam separation membrane.

A carbon dioxide collection and utilization system 100 includes a membrane reactor 10 and a regeneration unit 20. In the regeneration unit 20, a solid material in or on which carbon dioxide is absorbed or adsorbed is packed. When steam serving as a heat source is introduced into the regeneration unit 20 and the solid material is heated with the steam, the carbon dioxide is desorbed from the solid material. As a result, a gas containing carbon dioxide and steam is produced in the regeneration unit. At the same time, as a result of the carbon dioxide having removed therefrom, the solid material is regenerated.

The gas containing carbon dioxide produced in the regeneration unit 20 is introduced, through produced-gas introduction lines L21 and L22, from an introduction unit 12 of the membrane reactor 10 into the membrane reactor 10. A dehydration unit 50 is provided downstream of the produced-gas introduction lines L21 and L22. In the dehydration unit 50, the steam utilized for heating the solid material is removed, before being introduced into the membrane reactor 10, from the gas containing carbon dioxide. In addition, into the membrane reactor 10, hydrogen is introduced from the introduction unit 12 through a hydrogen introduction line L5.

The membrane reactor 10 includes a first space S1 on the pre-permeation side, a steam separation membrane 11, and a second space S2 on the post-permeation side. Into the first space S1, from the introduction unit 12, the gas containing carbon dioxide produced in the regeneration unit 20 and the hydrogen are introduced. The steam separation membrane 11 is an inorganic composite including a porous support 112 and an inorganic membrane 111 supported on the porous support 112. The porous support 112 is a porous cylindrical body having an outer circumferential surface (first surface) and an inner circumferential surface (second surface), and the first surface and the second surface communicate with each other through pores. The first space S1 communicates at the first surface with the pores. The second space S2 communicates at the second surface with the pores. In the first space S1, carrier particles P carrying a catalyst that promotes the hydrogenation reaction of carbon dioxide are packed.

A target product produced by the reaction in the first space S1 (at least one selected from the group consisting of synthetic fuel, methane, and methanol) is sent, together with unreacted gas, from a discharge unit 13 to a separation unit 40. In the separation unit 40, the target product (e.g., methanol) is separated from the unreacted gas. The separated unreacted gas is sent to the introduction unit 12 of the membrane reactor 10 through an unreacted-gas collection line L4, and is reused.

On the other hand, at least part of the steam produced in the first space S1 and part of the hydrogen introduced into the first space S1 permeate through the steam separation membrane 11 and move into the second space S2. Then, the steam and hydrogen in the second space S2 are sent to the regeneration unit 20 through a steam introduction line L1. Then, the heat of the steam and hydrogen is used in the regeneration unit 20 as at least part of the energy required for regenerating the solid material in or on which carbon dioxide is absorbed or adsorbed. Of the gases containing carbon dioxide produced in the regeneration unit 20, the steam is removed in the dehydration unit 50, and the carbon dioxide and hydrogen are sent to the first space S1 of the membrane reactor 10.

The regeneration unit 20 can also be used as a carbon dioxide collection unit 30 (hereinafter, a "collection unit 30"). A solid material that reversibly absorbs or adsorbs carbon dioxide is packed inside the regeneration unit 20 or the collection unit 30. During a predetermined period, the steam produced in the membrane reactor 10 is introduced into the regeneration unit 20 (collection unit 30) through the steam introduction line L1. During another period, a gas to be processed which contains carbon dioxide is introduced into the collection unit 30 (regeneration unit 20) through a gas-to-be-processed introduction line L3, and the carbon dioxide is collected. Gases containing components other than the carbon dioxide are discharged or transferred out of the system through a discharge line Lout.

In the system of FIG. 1, the regeneration unit 20 into which the steam and hydrogen are introduced is switched by operating a first branching part B1. The collection unit 30 into which the gas to be processed is introduced is switched by operating a second branching part B2. When a plurality of structures each of which serves as both the regeneration unit 20 and the collection unit 30 and accommodates the solid material are installed, the regeneration unit 20 and the collection unit 30 can be constantly secured in one system.

When superheated steam is used as the steam, since the relative humidity thereof is lower than that of saturated steam, the amount of condensed water that adheres to the surface of the solid material is reduced. The pressure of the superheated steam inside the regeneration unit 20 may be equal to or lower than the saturated steam pressure at the temperature of the solid material to be brought into contact with the superheated steam. The saturation temperature of the superheated steam may be set to a temperature which is about 10 to 15° C. lower than the temperature of the solid material to be brought into contact with the superheated steam. For example, when the temperature of the solid material is about 60° C., a superheated steam of about 70° C. with a saturation temperature of about 50° C. may be used.

INDUSTRIAL APPLICABILITY

The carbon dioxide collection and utilization system and the carbon dioxide collection and utilization method according to the present invention are suited, for example, for operating a carbon dioxide collection system in combination with a hydrogenation reaction of carbon dioxide in thermal power plants, cement factories, steel plants, chemical factories, and the like. Furthermore, the carbon dioxide collection and utilization system and the carbon dioxide collection and utilization method according to the present invention are excellent in energy efficiency, and therefore are suited for effectively utilizing the carbon dioxide collected by the DAC or in closed space, indoor space, and the like.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

REFERENCE SIGNS LIST

- 100: carbon dioxide collection and utilization system
  - 10: membrane reactor
    - 11: steam separation membrane
      - 111: inorganic membrane
      - 112: porous support
    - 12: introduction unit
    - 13: discharge unit
  - 20: regeneration unit
  - 30: carbon dioxide collection unit
  - 40: separation unit
  - 50: dehydration unit
- L1: steam introduction line
- L21, L22: produced-gas introduction line
- L3: gas-to-be-processed introduction line
- L4: unreacted-gas collection line
- L5: hydrogen introduction line
- Lout: discharge line
- S1: first space
- S2: second space
- P: catalyst particle
- B1: first branching part
- B2: second branching part

The invention claimed is:

1. A carbon dioxide collection and utilization system, comprising:

a regeneration unit that produces, from a solid material in or on which carbon dioxide is absorbed or adsorbed, a gas containing the carbon dioxide, and regenerates the solid material;

a reactor into which the gas containing the carbon dioxide produced in the regeneration unit and hydrogen are introduced and which produces steam and at least one selected from the group consisting of synthetic fuel, methane, and methanol; and a steam introduction line that introduces at least part of the steam produced in the reactor, into the regeneration unit.

2. The carbon dioxide collection and utilization system according to claim 1, wherein the reactor includes a first space on a pre-permeation side into which the gas containing the carbon dioxide and the hydrogen are introduced, a steam separation membrane, and a second space on a post-permeation side, wherein the steam and the hydrogen that have permeated through the steam separation membrane are introduced from the second space into the steam introduction line.

3. The carbon dioxide collection and utilization system according to claim 2, wherein the steam separation membrane is an inorganic composite including a porous support and an inorganic membrane supported on the porous support.

4. The carbon dioxide collection and utilization system according to claim 1, further comprising a dehydration unit that removes the steam from the gas containing the carbon dioxide before being introduced into the reactor.

5. The carbon dioxide collection and utilization system according to claim 1, further comprising a carbon dioxide collection unit that brings a gas to be processed which contains carbon dioxide into contact with the solid material, to allow the carbon dioxide to be absorbed in or adsorbed on the solid material, wherein the solid material in or on which carbon dioxide has been absorbed or adsorbed in the carbon dioxide collection unit is supplied to the regeneration unit.

6. A carbon dioxide collection and utilization method, comprising:

a preparation step of preparing a solid material in or on which carbon dioxide is absorbed or adsorbed, a regeneration step of producing from the solid material in or on which carbon dioxide is absorbed or adsorbed, a gas containing the carbon dioxide and regenerating the solid material; and a reaction step of allowing the gas containing the carbon dioxide to react with hydrogen, to produce steam and at least one selected from the group consisting of synthetic fuel, methane, and methanol, wherein the regeneration step includes bringing at least part of the steam into contact with the solid material in or on which carbon dioxide is absorbed or adsorbed.

7. The carbon dioxide collection and utilization method, according to claim 6, wherein in the reaction step, the gas containing the carbon dioxide and the hydrogen are introduced into a first space on a pre-permeation side of a reactor including the first space, a steam separation membrane, and a second space on a post-permeation side, and the steam and the hydrogen that have permeated through the steam separation membrane are extracted from the second space, and in the regeneration step, the steam and the hydrogen that have been extracted from the second space come in contact with the solid material in or on which carbon dioxide is absorbed or adsorbed.

* * * * *